United States Patent [19]

Rosenberger

[11] 4,187,005
[45] Feb. 5, 1980

[54] MICROSCOPE SUPPORT SYSTEM FOR USE IN EXAMINING EYES IN VIVO AND ENUCLEATED

[75] Inventor: Harold E. Rosenberger, Rochester, N.Y.

[73] Assignee: Bausch & Lomb Incorporated, Rochester, N.Y.

[21] Appl. No.: 953,231

[22] Filed: Oct. 20, 1978

[51] Int. Cl.² ............................................. A61B 3/00
[52] U.S. Cl. ........................................ 351/38; 351/39
[58] Field of Search ........................ 351/38, 39, 7, 16; 248/78; 128/745, 652; 354/62

[56] References Cited

U.S. PATENT DOCUMENTS 2,940,357  6/1960  Oswold .................................. 351/38

*Primary Examiner*—John K. Corbin
*Assistant Examiner*—Rodney B. Bovernick
*Attorney, Agent, or Firm*—Frank C. Parker; John S. Norton

[57] ABSTRACT

A system is provided for supporting and positioning a corneal endothelium microscope to permit: (1) examination of the corneal endothelium of an eye in vivo; and (2) examination of the corneal endothelium of an enucleated eye. The system includes a support mechanism for positioning the microscope relative to the eye in vivo, which mechanism includes means for moving the microscope in a horizontal direction into and out of engagement with the corneal epithelium of such eye. The system also includes apparatus for supporting the same microscope relative to the cornea of an enucleated eye which is positioned in a horizontal plane and for vertically adjusting the position of such cornea relative to the microscope.

8 Claims, 5 Drawing Figures

MICROSCOPE SUPPORT SYSTEM FOR USE IN EXAMINING EYES IN VIVO AND ENUCLEATED

BACKGROUND OF THE INVENTION

Corneal endothelium microscopes are used to examine and photograph the corneal endothelium of an eye in vivo. Such instruments often permit the detection of endothelium damage or disease which may not be seen by other ophthalmic instruments, such as a slit-lamp. Also, by use of such microscopes, the effects of, for instance, normal aging and trauma may be monitored. These instruments also have been recommended for use in the evaluation of surgical procedures. One such microscope and its use is described by W. M. Bourne, B. E. McCarey and H. E. Kaufman, "Clinical Specular Microscopy", *Journal of American Ophthalmology and Otolarynology*, OP 743-752, Vol. 81, Sept-Oct 1976.

When used to examine the corneal endothelium, the first element of the optical system of the microscope is brought into direct contact with the corneal epithelium. This is accomplished by securing the microscope to a support system which permits bidirectional horizontal adjustment as well as vertical adjustment. Basically, such a support system includes an adjustment knob for changing the vertical position of the microscope relative to the base of the support system. The base of such a system includes a control lever to effect movement in the horizontal direction. Typically, the control lever is connected to a spherical element which cooperates with a flat friction surface. Rotation of the spherical element, via movement of the control lever, relative to the friction surface produces bidirectional movement in the horizontal direction. Support systems using this type of mechanism are disclosed in U.S. Pat. Nos. 2,940,357, 3,914,032 and 3,944,342.

Prior to corneal surgery, it is desirable to examine the corneal endothelium of an enucleated eye to determine its condition and compare it with the corneal endothelium of the patient's damaged eye. The comparison may be made using two different microscopes, each with its own illumination and photographic systems. That is, the patient's eye would be examined in vivo as described above and the corneal endothelium of the enucleated eye examined using another microscope system. One method of examining the donor's eye is described by William M. Bourne, "Examination and Photography of Donor Corneal Endothelium", *Archives of Ophthalmology*, American Medical Association, Vol. 94, Oct. 1976, pp. 1799-1800.

In an alternate comparison method the enucleated eye is examined with the same microscope optical and illumination system as that used to examine the patient's eye. However, in this application, the enucleated eye is supported in a vertical position so that its orientation is similar to that which the patient's eye assumes under examination. This is a rather awkward position and requires special holding apparatus secured to a head rest to properly orient and support the enucleated eye so that no damage is inflicted thereto.

SUMMARY OF THE INVENTION

A system for supporting and positioning a microscope and its associated illumination system is provided for use in examining the corneal endothelium of an eye in vivo and the corneal endothelium of an enucleated eye. The system includes a head rest mechanism for maintaining the head of a patient in a fixed position. Cooperating with the head rest is apparatus for supporting and positioning the microscope with respect to the head rest. This apparatus also includes an adjusting mechanism to permit horizontal movement of the microscope with respect to the head rest and, hence, the eye in vivo. The system also includes apparatus for supporting the same microscope, and its associated illumination system, relative to an enucleated eye or the cornea therefrom which is positioned on a horizontal support. Apparatus is provided to vary the vertical distance between the microscope and the horizontal support. The system further includes first and second mounting means provided on the microscope.

Therefore, in view of the foregoing, it is an object of the present invention to provide a corneal endothelium microscope system utilizing the same optics and illumination for viewing both an eye in vivo and an enucleated eye.

It is also an object of this invention to provide a corneal endothelium microscope system which is readily transferred from a horizontal support to a vertical support.

It is a further object of this invention to provide a corneal endothelium microscope system wherein the in vivo eye and the enucleated eye being examined are both supported in the most acceptable manner for examining purposes.

DESCRIPTION OF THE PREFERRED EMBODIMENT

Figure 1:
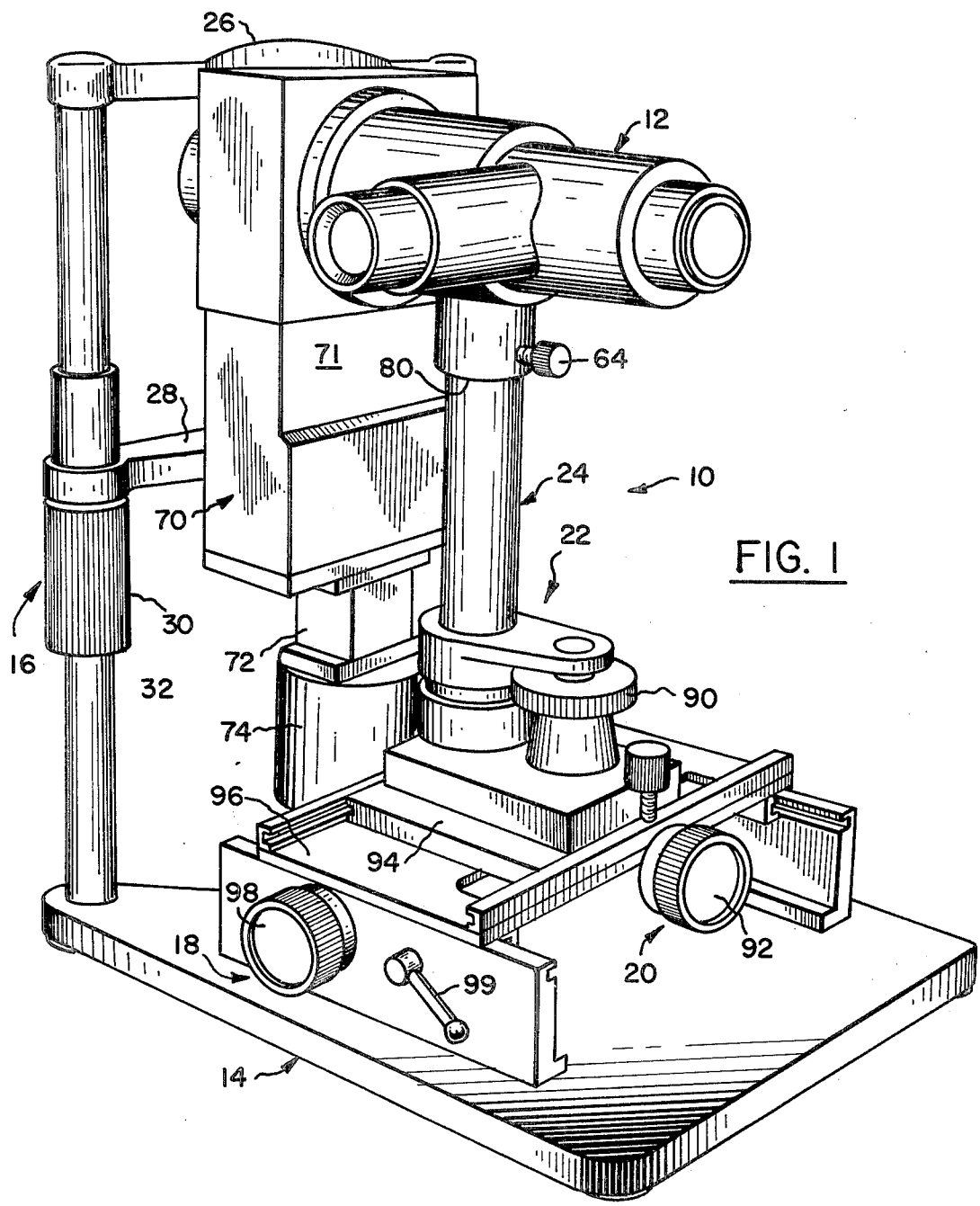
FIG. 1 is a perspective view of a tridirectional mounting system for a corneal endothelium microscope.

As best seen in FIG. 1, a system 10 is shown for supporting and positioning a corneal endothelium microscope 12. The system 10 generally includes a base 14, head rest supporting assembly 16, x-axis adjusting mechanism 18, y-axis adjusting mechanism 20, z-axis adjusting mechanism 22 and support member 24.

Figure 2:
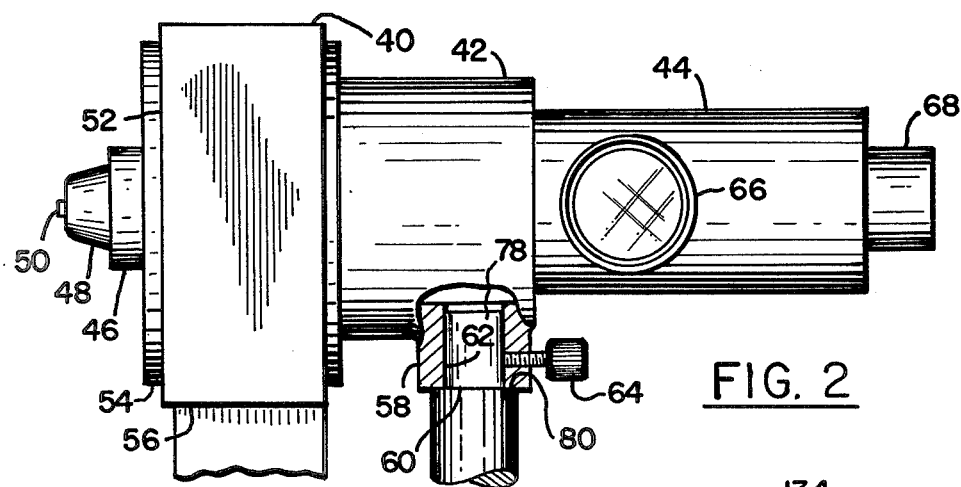
FIG. 2 is a partial side view of the microscope and support system of FIG. 1.
Figure 3:
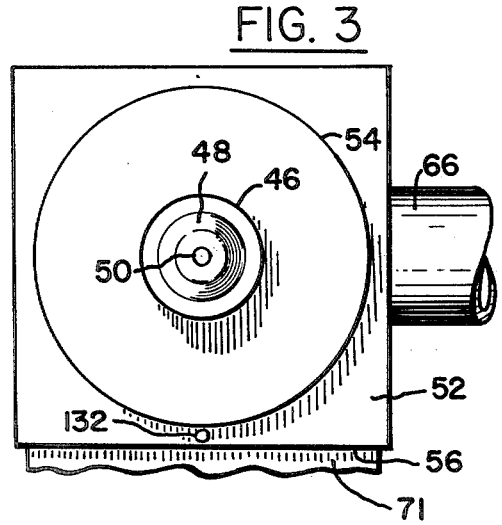
FIG. 3 is a front view of the microscope.

The endothelium microscope 12 includes a front housing section 40, a central housing section 42 and a rear housing section 44. As illustrated in FIG. 2, attached to the front end of housing section 40 is nosepiece housing 46 including objective support housing 48 which, in turn, supports corneal contact element 50. Housing section 40 also includes the front mounting surface 52 and an alignment flange 54. Finally, front housing section 40 includes a lower mounting surface 56. Central housing section 42 includes a cylindrical sleeve portion 58 having a mounting surface 60 and a cylindrical bore 62. Sleeve 58 is drilled and taped to receive the threads of thumb screw 64. Rear housing section 44 includes an end portion 66 which is adapted to accept an eyepiece (not shown) and a cylindrical end portion 68 for supporting a camera (also not shown).

Though not illustrated in the drawings, microscope 12 includes a focusable objective and a relay lens system which form an image of the corneal endothelium in the eyepiece focal plane. These elements are positioned along the optical axis behind corneal contact plate 50. The optical system also includes a half aperture reflector for combining the optical axis of microscope 12 with the optical axis of illumination and flash system 70. The optical system further includes a beam divider whereby the image formed by the objective can be simultaneously viewed with an eyepiece (not shown) as well as photographed. Finally, though also not illustrated in the drawings, housing section 44 is rotatably received within housing section 42 for movement from a first position, as shown in FIGS. 1 and 2 to second position in which end portion 66 is facing in the opposite direction. This arrangement permits instrument 10 to be operated from either side without the nose of the patient interfering with the operator's line of sight when the corneal contact element 50 is moved horizontally into contact with the corneal epithelium.

Illumination and flash system 70, secured to mounting surface 56 of housing section 40, includes a housing 71, flash unit 72 and an illuminator 74, all as illustrated in FIG. 1. Supported within housing 71 are various optical components (not shown) which form an image of the filament of the lamp (also not shown) housed in illuminator 74, in the back focal plane of the objective of microscope 12 for illuminating the corneal endothelium. This optical system also forms an image of the flash, generated in flash unit 72, in the back focal plane of the objective of microscope 12 for directing a flash on the corneal endothelium for photographic purposes.

In order to couple microscope 12 with position adjusting mechanisms 18, 20 and 22 for movement along x, y and z-axes, the support post 24 has a reduced upper end 78 which is received within bore 62 of cylindrical sleeve portion 58 with shoulder 80 in engagement with mounting surface 60. To prevent both disengagement and rotation of microscope 12 about support post 24, thumb screw 64 is turned inwardly to thereby exert pressure against end 78.

In order to examine a corneal endothelium in vivo, a patient's head is held by head rest 26 and chin supporting bar 28 of assembly 16 relative to microscope 12. The position of bar 28 may be vertically adjusted by rotating adjusting knob 30 having internal threads (not shown) relative to external threads (also not shown) provided on upright support rod 32.

With the patient's head properly positioned, the position of microscope 12 is adjusted. Vertical or z-axis adjustment is accomplished by rotation of knob 90 which raises or lowers support member 24. The lateral position of the microscope 12 is adjusted by rotation of knob 92, of y-axis adjusting mechanism 20, which moves table 94. Finally, table 96 and, hence, microscope 12, is moved along the x-axis (directly towards the eye in vivo) by rotating knob 98 of mechanism 18. When corneal contact element 50 is brought into engagement the position of table 96 relative to base 14 is fixed by a locking mechanism actuated by rotation of lever 99 and the corneal endothelium examined and, if desired photographed by a camera (not shown) secured to end portion 68. A detailed description of adjusting mechanisms 18, 20 and 22 is set forth in cofiled application Ser. No. 953,731 (Bausch & Lomb Case: Peck 10) the disclosure of which is incorporated herein by reference.

Figure 5:
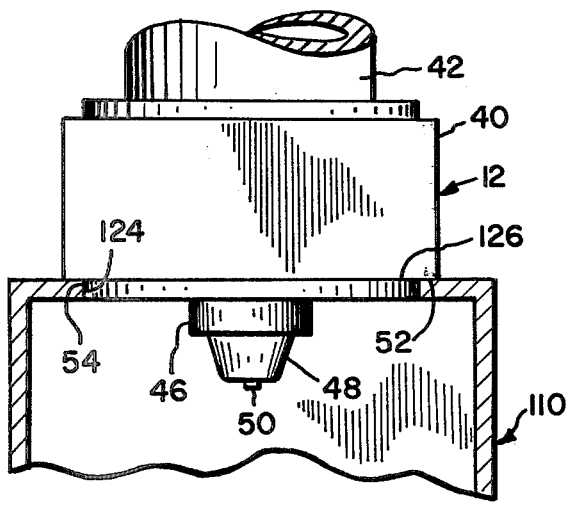
FIG. 5 is a cross-sectional view taken along lines 5—5 of FIG. 4 and showing the microscope in place.
Figure 4:
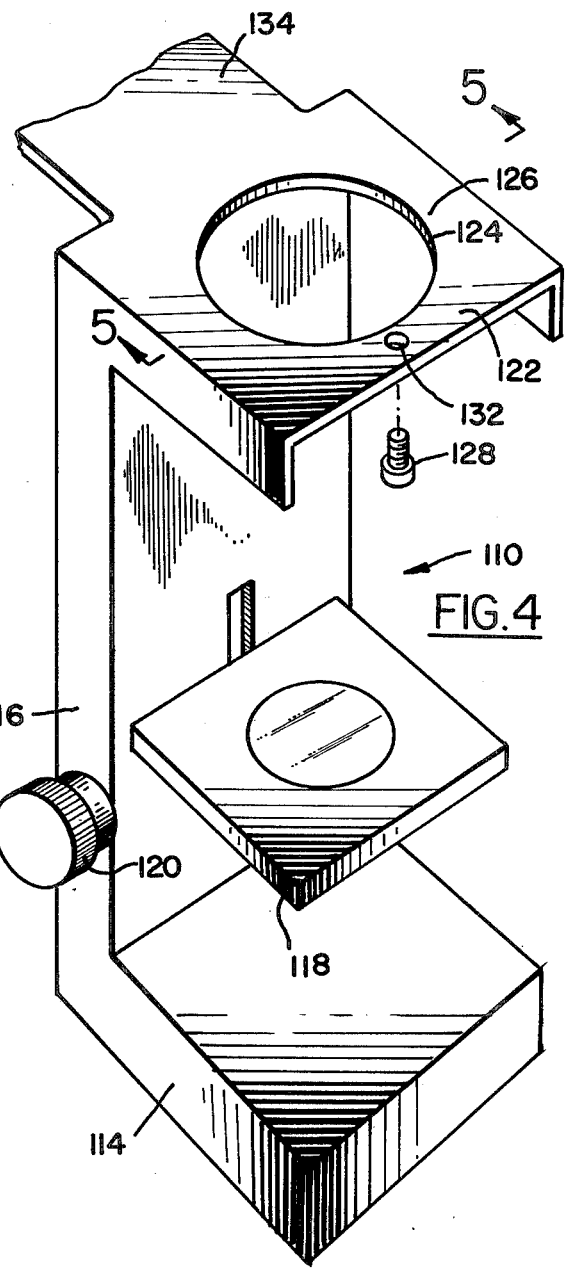
FIG. 4 is a perspective view of a vertical support system for the microscope.

In, for instance, corneal transplant surgery, it is desirable to examine the endothelium of the prospective transplant cornea to determine its condition and compare it with the corneal endothelium of the patient's damaged eye. According to the present invention, this is accomplished by loosening thumb screw 64 (FIGS. 1 and 2), lifting microscope 12 off post 24 and transferring it to microscope support system 110, schematically illustrated in FIG. 4. This may, most conveniently, be accomplished by use of the base, stand and stage assembly of the microscope manufactured and sold by applicant's assignee under the BALPLAN trademark. With reference to FIGS. 4 and 5, microscope support system 110 includes a base 114, a support arm 116, a stage 118, apparatus (not shown) coupled to adjusting knob 120 for moving the stage 118 in the vertical of z-direction and a microscope mounting flange 122.

The microscope mounting flange 122 has an aperture 124 formed therethrough the diameter of which is adapted to closely receive alignment flange 54 on front housing section 40 of microscope 12, as illustrated in FIG. 5. In this position, the front mounting surface 52 of front housing section 40 is in engagement with top surface 126 of flange 122. Any appropriate means for securing the microscope 12 to the support apparatus 110 may be used, such as locking screw 128 which passes through aperture 130 in the flange 122 and is received by threaded aperture 132 in the front mounting surface 52.

With reference to FIG. 4 and, depending upon the length and weight of the illumination and flash system 70, it may be desirable to lengthen top surface 126 by providing an extension 134 to permit system 70 to also be supported. Alternatively, a BALPLAN microscope stand may be utilized.

In operation, the enucleated eye or the cornea therefrom to be examined is placed on the stage 118 of the support apparatus 110. As an enucleated eye may be easily supported in the horizontal plane of stage 118, no special apparatus is needed to suspend the eye in a vertical manner as required by the prior art. Stage 118 is then adjusted to bring the epithelium of the cornea into contact with corneal contact element 50 of microscope 12.

Use of the same microscope 12, together with illumination and flash system 70 not only saves duplicative costs required when two microscopes are utilized but also eliminates the possibility of discrepancies which may result from the use of two different microscopes and their amounted illumination systems. Unnatural and cumbersome vertical mounting of an enucleated eye is also avoided.

Whereas the drawings and accompanying description have shown and described the preferred embodiment of the present invention, it should be apparent to those skilled in the art that various changes may be made in the form of the invention without affecting the scope thereof.

I claim:

1. A system for supporting and positioning a microscope to permit both the examination of the cornea of an eye in vivo and the examination of an enucleated eye with the same optical and illumination systems, said optical system including a corneal contact element, said system comprising:
    (a) a head rest mechanism for supporting and positioning a head to thereby position an eye in vivo in a fixed location;
    (b) a first means for supporting and positioning said microscope relative to said head rest mechanism, said first means including means for moving said microscope toward and away from said head rest mechanism to thereby permit said corneal contact element to be brought into and out of contact with the cornea of an eye in vivo;
(c) means for supporting an enucleated eye in a substantially horizontal plane;
(d) a second means for supporting and positioning said microscope relative to said enucleated eye support; and
(e) means for varying the relative distance between said microscope and said enucleated eye support to thereby permit said corneal contact element to be brought into and out of contact with the cornea of an enucleated eye for microscopic examination thereof.

2. The system as described in claim 1 further including a microscope and wherein said microscope includes first and second mounting means, said first mounting means cooperating with said first supporting and positioning means, said second mounting means cooperating with said second supporting and positioning means.

3. The system as described in claim 2 wherein said first mounting means includes a cylindrical sleeve adapted to receive a complimenting tubular post supported on said first supporting and positioning means.

4. The system as described in claim 3 wherein said first mounting means also includes means for detachably engaging said microscope to said tubular post.

5. The system as described in claim 2 wherein said second mounting means includes an annular flange and an alignment surface and wherein said second supporting and positioning means includes a support surface for cooperation with said alignment surface and an annular recess for cooperation with said annular flange.

6. The system as described in claim 5 wherein said support surface includes a section which, when said annular flange is received in said annular recess and said alignment surface is in engagement with said support surface, lies beneath the illumination system of said microscope and may be used to provide support for said illumination system.

7. The system as described in claim 5 wherein said second mounting means includes means for detachably engaging said microscope to said second supporting and positioning means.

8. The method of comparing the corneal endothelium of an eye in vivo with the corneal endothelium of an enucleated eye, comprising the steps of:
(a) mounting a corneal endothelium microscope having a corneal contact element to a first support system in a substantially horizontal plane;
(b) moving, in a substantially horizontal direction, said corneal contact element into engagement with the cornea of an eye in vivo;
(c) observing the corneal endothelium of an eye in vivo with said microscope;
(d) removing said microscope from said first support system;
(e) placing said microscope in a second support system for movement in a substantially vertical manner, said support system having a support for an enucleated eye or the cornea therefrom; and
(f) examining the corneal endothelium of an enucleated eye with said microscope for comparison to the corneal endothelium of said eye in vivo.

* * * * *

UNITED STATES PATENT AND TRADEMARK OFFICE
CERTIFICATE OF CORRECTION

PATENT NO. : 4,187,005
DATED : February 5, 1980
INVENTOR(S) : Harold E. Rosenberger It is certified that error appears in the above–identified patent and that said Letters Patent are hereby corrected as shown below:

Column 3, line 62, after No. delete "953,731" and substitute therefor --953,232--.

Signed and Sealed this

Third Day of February 1981

[SEAL]

Attest:

RENE D. TEGTMEYER

Attesting Officer

Acting Commissioner of Patents and Trademarks